United States Patent
Conlon et al.

(10) Patent No.: US 7,374,557 B2
(45) Date of Patent: May 20, 2008

(54) SUBCUTANEOUS SELF ATTACHING INJECTION PORT WITH INTEGRAL FASTENERS

(75) Inventors: Sean P. Conlon, Loveland, OH (US); Ronald John Kolata, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 637 days.

(21) Appl. No.: 10/741,868

(22) Filed: Dec. 19, 2003

(65) Prior Publication Data

US 2004/0254536 A1  Dec. 16, 2004

Related U.S. Application Data

(60) Provisional application No. 60/478,763, filed on Jun. 16, 2003.

(51) Int. Cl.
*A61M 5/32* (2006.01)
(52) U.S. Cl. ...................................... 604/175
(58) Field of Classification Search ............... 604/175, 604/174, 288.01, 523, 93.01; 606/72, 75, 606/175
See application file for complete search history.

(56) References Cited

U.S. PATENT DOCUMENTS

| | | | |
|---|---|---|---|
| 4,665,906 A | | 5/1987 | Jervis |
| 4,673,394 A | * | 6/1987 | Fenton et al. ............... 604/175 |
| 4,772,261 A | * | 9/1988 | Von Hoff et al. ........... 604/507 |
| 4,898,585 A | | 2/1990 | Borsanyi et al. |
| 4,925,445 A | | 5/1990 | Sakamoto et al. |
| 4,976,715 A | * | 12/1990 | Bays et al. .................... 606/77 |
| 5,174,487 A | | 12/1992 | Rothfuss et al. |
| 5,203,864 A | | 4/1993 | Phillips |
| 5,207,644 A | | 5/1993 | Strecker |
| 5,213,574 A | | 5/1993 | Tucker |
| 5,217,486 A | | 6/1993 | Rice et al. |
| 5,246,156 A | | 9/1993 | Rothfuss et al. |
| 5,261,914 A | * | 11/1993 | Warren ........................ 606/73 |
| 5,281,199 A | | 1/1994 | Ensminger et al. |
| 5,290,297 A | | 3/1994 | Phillips |
| 5,318,545 A | | 6/1994 | Tucker |
| 5,332,398 A | * | 7/1994 | Miller et al. ................. 604/175 |
| 5,333,772 A | | 8/1994 | Rothfuss et al. |

(Continued)

FOREIGN PATENT DOCUMENTS

DE 197 45 654 4/1999

(Continued)

OTHER PUBLICATIONS

U.S. Appl. No. 11/166,610, filed Jun. 24, 2005, Uth et al.

(Continued)

Primary Examiner—Nicholas D. Lucchesi
Assistant Examiner—Christopher D Koharski
(74) Attorney, Agent, or Firm—Frost Brown Todd, LLC

(57) ABSTRACT

A self attaching injection port has integral fasteners extending from the housing, fixed relative thereto. The fasteners include one way fasteners, such as formed by a plurality of axially spaced concentrically aligned frustroconical annular flanges. The injection port is self attaching upon the surgeon applying a distal force to the injection port housing, causing the fasteners to penetrate the tissue, engaging the tissue to hold the injection port in place.

12 Claims, 2 Drawing Sheets

U.S. PATENT DOCUMENTS

| | | |
|---|---|---|
| 5,350,360 A | 9/1994 | Ensminger et al. |
| 5,381,943 A | 1/1995 | Allen et al. |
| 5,387,192 A | 2/1995 | Glantz et al. |
| 5,399,168 A | 3/1995 | Wadsworth, Jr. et al. |
| 5,417,656 A | 5/1995 | Ensminger et al. |
| 5,470,010 A | 11/1995 | Rothfuss et al. |
| 5,503,630 A | 4/1996 | Ensminger et al. |
| 5,527,277 A | 6/1996 | Ensminger et al. |
| 5,527,278 A | 6/1996 | Ensminger et al. |
| 5,558,641 A | 9/1996 | Glantz et al. |
| 5,582,616 A | 12/1996 | Bolduc et al. |
| 5,588,581 A | 12/1996 | Conlon et al. |
| 5,601,224 A | 2/1997 | Bishop et al. |
| 5,613,945 A | 3/1997 | Cai et al. |
| 5,632,729 A | 5/1997 | Cai et al. |
| 5,634,584 A | 6/1997 | Okorocha et al. |
| 5,637,102 A | 6/1997 | Tolkoff et al. |
| 5,688,247 A | 11/1997 | Haindl et al. |
| 5,718,682 A | 2/1998 | Tucker |
| 5,743,873 A | 4/1998 | Cai et al. |
| 5,792,104 A | 8/1998 | Speckman et al. |
| 5,792,123 A | 8/1998 | Ensminger et al. |
| 5,810,882 A | 9/1998 | Bolduc et al. |
| 5,817,062 A | 10/1998 | Flom et al. |
| 5,829,662 A | 11/1998 | Allen et al. |
| 5,830,221 A | 11/1998 | Stein et al. |
| 5,871,532 A | 2/1999 | Schroeppel |
| 5,954,687 A | 9/1999 | Baudino et al. |
| 5,976,159 A | 11/1999 | Bolduc et al. |
| 6,086,555 A | 7/2000 | Eliasen et al. |
| 6,213,973 B1 | 4/2001 | Eliasen et al. |
| 6,319,226 B1 | 11/2001 | Sherry |
| 6,447,524 B1 | 9/2002 | Knodel et al. |
| 2002/0013557 A1 | 1/2002 | Sherry |
| 2002/0198548 A1 | 12/2002 | Robert |
| 2004/0220682 A1 | 11/2004 | Levine et al. |
| 2004/0249362 A1 | 12/2004 | Levine et al. |
| 2004/0254537 A1 | 12/2004 | Conlon et al. |
| 2005/0131352 A1 | 6/2005 | Conlon et al. |

FOREIGN PATENT DOCUMENTS

| | | |
|---|---|---|
| DE | 197 51 791 | 5/1999 |
| EP | 1057457 A1 | 12/2000 |
| EP | 1 488 824 | 12/2004 |
| WO | WO 99/34859 | 7/1999 |
| WO | WO 2005/037055 | 4/2005 |

OTHER PUBLICATIONS

U.S. Appl. No. 11/166,625, filed Jun. 24, 2005, Uth et al.

* cited by examiner

SUBCUTANEOUS SELF ATTACHING INJECTION PORT WITH INTEGRAL FASTENERS

RELATED APPLICATIONS

This application claims the priority of provisional patent application Ser. No. 60/478,763, titled Fluid Injection Port For Adjustable Gastric Band, filed on Jun. 16, 2003, the disclosure of which is incorporated herein by reference. This application also incorporates by reference the following co-pending United States Patent Applications filed of even date herewith: application Ser. No. 10/741,127 (Subcutaneous Injection Port For Applied Fasteners, inventors: Conlon and Hunt), pending; and application Ser. No. 10/741,875, (Subcutaneous Self Attaching Injection Port With Integral Moveable Retention Members, inventors: Conlon, Byrum, Hunt, Nuchols and Schulze), pending.

TECHNICAL FIELD

The present invention relates in general to surgically implantable fluid injection ports, and is particularly directed to fasteners and methods for fastening subcutaneous peripherally attached ports. The invention will be specifically disclosed in connection with injection ports used with adjustable gastric bands, although the fasteners of the present invention may be used with many different subcutaneously attached devices, including injection ports used for vascular access such as the infusion of medications and blood draws.

BACKGROUND OF THE INVENTION

Injection ports are placed beneath the skin of a body for injecting fluids into the body, such as for infusing medication, blood draws, and many other applications, including adjustable gastric bands. Since the early 1980s, adjustable gastric bands have provided an effective alternative to gastric bypass and other irreversible surgical weight loss treatments for the morbidly obese. The gastric band is wrapped around an upper portion of the patient's stomach, forming a stoma that restricts food passing from an upper portion to a lower portion of the stomach. When the stoma is of the appropriate size, food held in the upper portion of the stomach provides a feeling of fullness that discourages overeating. However, initial maladjustment or a change in the stomach over time may lead to a stoma of an inappropriate size, warranting an adjustment of the gastric band. Otherwise, the patient may suffer vomiting attacks and discomfort when the stoma is too small to reasonably pass food. At the other extreme, the stoma may be too large and thus fail to slow food moving from the upper portion of the stomach, defeating the purpose altogether for the gastric band.

In addition to a latched position to set the outer diameter of the gastric band, adjustability of gastric bands is generally achieved with an inwardly directed inflatable balloon, similar to a blood pressure cuff, into which fluid, such as saline, is injected through a fluid injection port to achieve a desired diameter. Since adjustable gastric bands may remain in the patient for long periods of time, the fluid injection port is typically installed subcutaneously to avoid infection, for instance in front of the sternum. Adjusting the amount of fluid in the adjustable gastric band is achieved by inserting a Huber needle through the skin into a silicon of the injection port. Once the needle is removed, the septum seals against the hole by virtue of compressive load generated by the septum. A flexible conduit communicates between the injection port and the adjustable gastric band.

The traditional surgical technique for securing a fluid injection port developed for vascular uses has been applying sutures through a series of holes spaced about a peripheral base flange. While generally effective, suturing often proves to be difficult and time consuming, even more so with adjustable gastric band which are intended for the morbidly obese. A significant thickness of fat tissue may underlie the skin, causing difficulties as the surgeon attempts to apply sutures to deeply recessed tissues (e.g., 5-10 cm) to secure the port, often requiring 10-15 minutes to complete. Further, if the injection port is not sutured properly, the port may flip over, making subsequent injections difficult or impossible.

Recently, a surgical stapler has been described in a German patent application No. 197 51 791.9 to Pier wherein a hat-shaped injection port includes tangentially aligned linear grooves spaced around its perimeter. A pair of holes in each linear groove receives a traditional bent wire staple. A stapler holds the staples in place and has downwardly moving forming member that presses upon the shoulders of each staple. Due to the position of the holes in the linear groove, pointed ends of the staple are deformed inwardly to grip underlying tissue.

This Pier stapler thus attaches the staples through a deformation that may prove difficult to release should the initial placement be undesirable or removal of the gastric band be appropriate. Further, because the device must permanently deform a multiplicity of stainless steel or titanium staples, a more complicated mechanism is required to provide the surgeon with enough mechanical advantage to form the staples easily. The Pier injection port also requires a custom stapler handle that is not useful for any other purpose, which may be an undesirable expense for surgeons who do not perform numerous placements of the Pier injection port.

While a custom stapler for an injection port may have advantages over suturing, such as the time required to accomplish the attachment, it is believed that other approaches to attaching an injection port may have additional advantages or features not provided by traditional suturing or a stapler using bent wire staples.

Consequently, a significant need exists for a fluid injection port suitable for subcutaneous attachment that is quickly attachable yet is secure over a long period of time.

BRIEF SUMMARY OF THE INVENTION

As described herein, there is provided an injection port for injecting fluids into a body. The port includes a housing for placement beneath the skin of the body, and means for receiving a needle. An attachment mechanism is provided which is configured to engage tissue surrounding the housing to retain the housing in place. The attachment is integrally attached to and fixed relative to the housing. A plurality of fasteners including retention members in the form of frustroconical flanges which function as one-way fasteners to resist withdrawal of the fasteners and resist unwanted movement of the injection port.

BRIEF DESCRIPTION OF THE DRAWINGS

The accompanying drawings incorporated in and forming a part of the specification illustrate several aspects of the present invention, and together with the description serve to explain the principles of the invention. In the drawings.

Reference will now be made in detail to the present preferred embodiment of the invention, an example of which is illustrated in the accompanying drawings.

DETAILED DESCRIPTION OF AN EMBODIMENT OF THE PRESENT INVENTION

Figure 1:
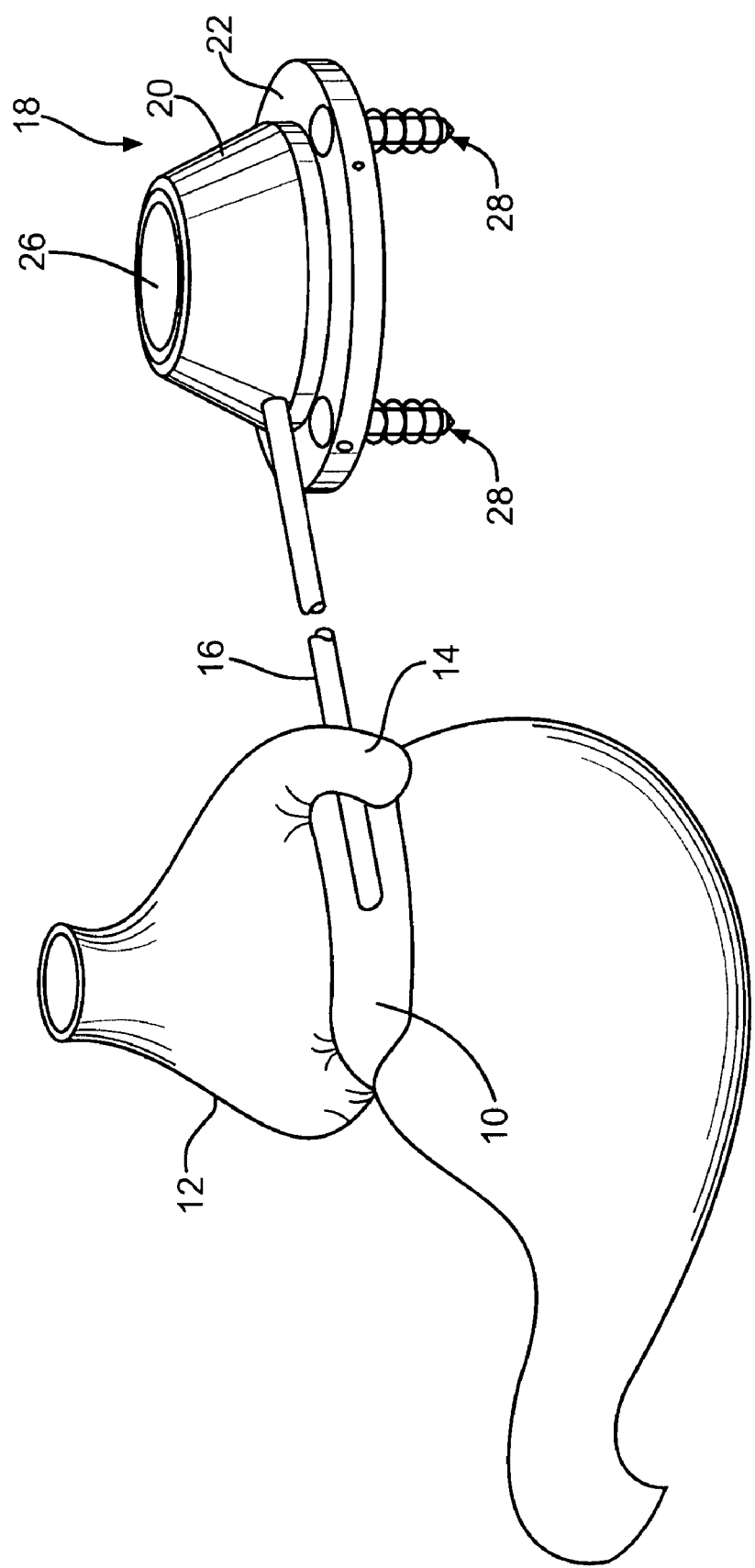
FIG. 1 is a diagrammatic drawing showing an injection port constructed in accordance with the present invention, connected to an adjustable gastric band wrapped around an upper part of a stomach.

Referring now to the drawings in detail, wherein like numerals indicate the same elements throughout the views, FIG. 1, adjustable gastric band 10 is shown wrapped around an upper portion of stomach 12, kept in place by attaching the two ends together and extending portion 14 of the stomach 12 over adjustable gastric band 10 by suturing portion 14 to the stomach. One end of flexible conduit 16 is in fluid communication with the internal cavity of the balloon (not shown), with the other end being in fluid communication with an internal cavity of injection port 18. At the time adjustable gastric band 10 is implanted around a portion of the stomach, remote injection port 18 is also implanted at a suitable location, usually within the rectus sheaths, for transcutaneous access via a Huber needle.

As is well known, injection port 18 includes housing 20 having annular flange 22 extending outwardly from one end. Nipple 24 is in fluid communication with the internal cavity defined by housing 20, to which flexible conduit 16 is attached at some point in the procedure, typically after injection port 18 has been implanted. Fluid is added to or removed from the interior cavity of injection port 18 by inserting a Huber needle percutaneously into silicone septum 26 of the injection port 18. Although septum 26 is made of silicon, the means of the injection port for receiving a needle includes any structure configured to self seal after puncture with a non-coring needle.

Although a specific configuration for injection port 18 is disclosed herein, there are many suitable configurations which may be used in conjunction with the present invention.

Figure 2:
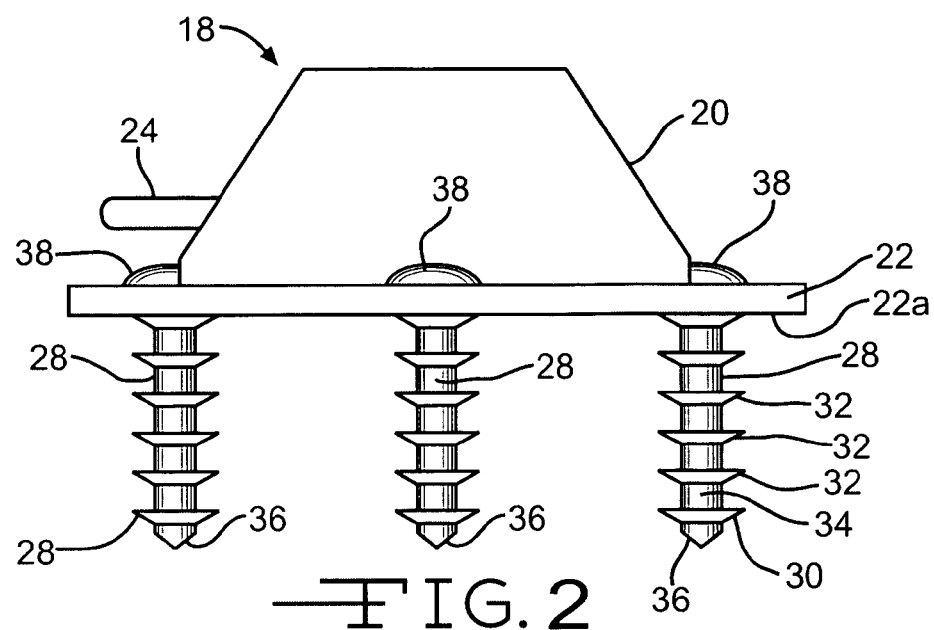
FIG. 2 is a side view of the injection port shown in FIG. 1.
Figure 3:
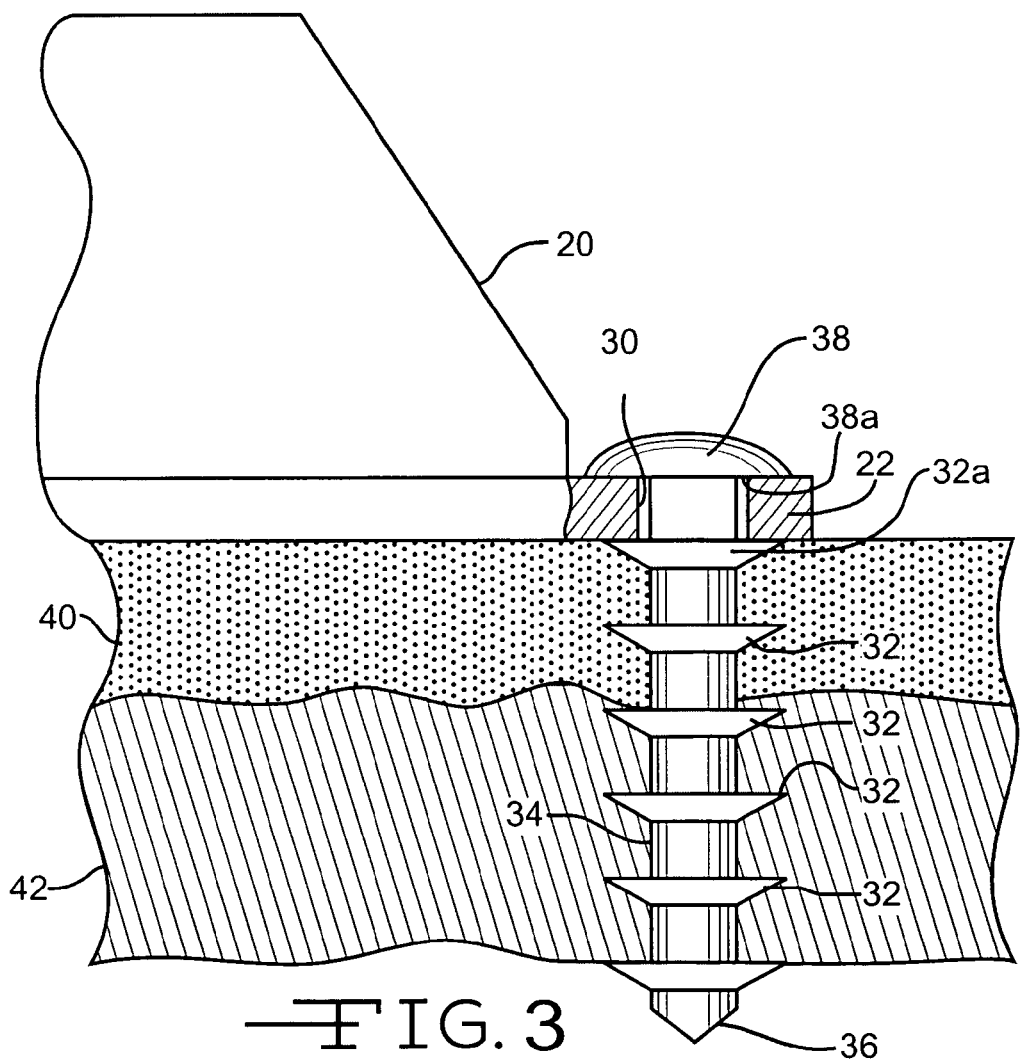
FIG. 3 is an enlarged, fragmentary side view of the injection port shown in FIG. 1.

Referring also to FIGS. 2 and 3, injection port 18 includes integral fasteners 28 extending distally from housing 20. Fasteners 28 are disposed through circumferentially spaced holes 30 (see FIG. 3) formed in flange 22 of housing 20. The teachings of this invention may be practiced with a smaller flange, or no flange, such as may be accomplished by forming recesses in the side of housing 20 surrounding holes formed through the base. Three fasteners 28 are effective to prevent injection port 18 from flipping over after implantation, such as due to passive or induced movements of the patient. However, the present invention is not limited to the use of three fasteners, and one or more fasteners may be used.

The integral fasteners 28 illustrated in FIGS. 1-3 are one way fasteners. As used herein, a one way fastener is one which is configured to be inserted into and engage the fascia or other layer, and resist withdrawal therefrom. Although there are many different structures which can provide such one way functionality, such as outwardly extending axially and circumferentially spaced fingers, the one way function of the embodiment of fasteners 28 illustrated results from a plurality of frustroconical annular flanges 32 axially spaced along shaft portion 34. Tip 36, which is illustrated with inclined surfaces, is formed at the distal end of shaft portion 34, with head portion 38 disposed at the other end. It is noted that tip 36 may have any shape, although a shape configured to facilitate penetration of the fascia or other layer reduces the force necessary to deploy/implant injection port 18.

Flanges 28 could alternatively be flat spaced apart flanges, presenting resistance to withdrawal due to the nature of the tissue, but also presenting increased resistance to insertion than with the rearwardly sloping surfaces of the frustroconical shape.

In the embodiment illustrated, head portion 38 is larger than hole 30 and thus configured not to pass through the opening 30. Prior to deployment/implantation of injection port 18, fasteners 28 are attached to housing 20 integrally by inserting them through holes 30. Flanges 32 may be sufficiently deformable to yield inwardly when passed through hole 30. Additionally flanges 32 may be discontinuous about their respective circumferences, such as having a slot extending the length of shaft 34. Flange 32a retains fastener 28 in hole 30 attached to and fixed relative to housing 20, flange 32a being axially spaced from lower surface 38a of head portion 38 a distance sufficient for flange 32a to expand after being pushed through hole 30, and engage lower surface 22a of flange 22 adjacent hole 30, thereby resulting in fasteners 28 being integral with injection port 18 prior to deployment. There may be radial clearance between hole 30 and shaft portion 34 or axial clearance between lower surface 38a and flange 32a.

Although fasteners 28 may be attached to injection port 18 at any point prior to or at the time of deployment, it is contemplated that injection port 18 will be provided to the surgeon with the integral fasteners 28 pre-attached, as a sterilized assembly.

Implantation of self attaching injection port 18 is accomplished by locating injection port 18 in the desired location and applying a distal force to housing 20, or even head portions 38, of injection port 18 thereby causing tips 36 of fasteners 28 to engage the adjacent tissue, penetrating fat layer 40 and fascia layer 42 in the illustration. The parallel angles of frustroconical flanges 32 toward head portion 38 allow fasteners 28 to penetrate and advance through fat layer 40 and fascia layer 42, and to lock thereagainst to resist withdrawal.

Operating as concentric, axially spaced locking rings, flanges 32 retain injection port 18 in position.

Fastener 28 may be made of any suitable medically compatible material having sufficient resilience and strength to perform as described herein, such as polycarbonate, polystyrene, or any suitable polymer. The quantity, spacing, and dimensions of flanges 32 may be any quantity, spacing and dimensioning as are suitable. By way of example only, the center to center distance of flanges 32 may be 3 mm, the thickness (at the shaft) may be 1 mm, and the diameter may be 3 mm, with the shaft 5 mm long.

In summary, numerous benefits have been described which result from employing the concepts of the invention. The foregoing description of one or more embodiments of the invention has been presented for purposes of illustration and description. It is not intended to be exhaustive or to limit the invention to the precise form disclosed.

Obvious modifications or variations are possible in light of the above teachings. For example, one or more fasteners with one or more frustroconical flanges may be installed through on into appropriately shaped openings in the injection port at the time of implantation, such as by locating the injection port in the appropriate position in the body and inserting the fasteners through the openings.

The one or more embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. An injection port implantable within a body and for injecting fluids therein, said port comprising:
 a. a housing for placement beneath the skin of the body, said housing having a distal side for placement on tissue, a proximal side including a septum for receiving a needle therein, and a longitudinal axis extending between the distal side and the proximal side, wherein said housing further comprises at least two openings extending distally to proximally through said housing, wherein the openings are annularly spaced adjacent a periphery of the housing;
 b. a flexible conduit having a first end in fluid communication with the housing; and
 c. an attachment mechanism comprising a plurality of fasteners, wherein each fastener extends distally from the distal side of said housing through an opening of the at least two openings of said housing, wherein each fastener is formed from a non-biodegradable material, wherein each fastener is configured to engage soft tissue surrounding said housing so as to secure said housing in place, each fastener being integrally attached to and fixed relative to said housing, wherein each fastener comprises:
  i) a solid elongated shaft disposed through an opening of the at least two openings of said housing,
  ii) a head at a proximal end of the elongated shaft, the head being adjacent to and larger than a proximal end of the opening through which the elongated shaft is disposed, to prevent distal movement of the head through the opening,
  iii) a capture member on the elongated shaft, spaced distally from the head, wherein the capture member is configured to expand after being pushed proximally to distally through the opening through which the elongated shaft is disposed, wherein the capture member is configured to expand to a size larger than a distal end of the opening to engage against the distal side of said housing to integrally secure the fastener relative to the housing,
  iv) a piercing tip at a distal end of said the elongated shaft, wherein the piercing tip has a point configured to penetrate through soft tissue, and
  v) one or more retention members along the elongated shaft, between the capture member and the point of the piercing tip, wherein the one or more retention members are configured to be inserted into soft tissue and to resist removal from the soft tissue.

2. The port of claim 1, wherein said attachment mechanism is configured such that by applying a distal force to said housing, said attachment mechanism will engage said tissue so as to retain said housing.

3. The port of claim 1, wherein each of said one or more retention members of each fastener comprises at least one outwardly extending flange spaced from said elongated shaft.

4. The port of claim 3, wherein said at least one flange comprises a plurality of spaced apart flanges.

5. The port of claim 3, wherein said at least one flange has a frustroconical shape.

6. The port of claim 3, wherein said at least one flange is discontinuous.

7. The port of claim 3, wherein said at least one fastener comprises at least one outwardly extending finger spaced from said housing.

8. The port of claim 7, wherein said at least one finger comprises a plurality of spaced apart fingers.

9. The port of claim 1, wherein said housing includes an annular flange extending circumferentially about said longitudinal axis, wherein the annular flange is at said distal side of said housing, said at least two openings being formed in said annular flange.

10. The port of claim 1, wherein said attachment mechanism is constructed from materials that remain secured for the duration of the implant.

11. The port of claim 1, wherein said attachment mechanism is formed from a thermoplastic implantable within the body.

12. The port of claim 11, wherein said attachment mechanism is formed from at least one material selected from the group consisting of polycarbonate and polystyrene.

* * * * *